United States Patent [19]

Maubru

[11] Patent Number: 6,136,042
[45] Date of Patent: Oct. 24, 2000

[54] DIRECT CAPILLARY DYEING COMPOSITION COMPRISING A CROSS-LINKED POLYMER WITH ACRYLIC AND ALKYL $C_{10}$-$C_{30}$ ACRYLATE UNITS

[75] Inventor: Mireille Maubru, Chatou, France

[73] Assignee: L'Oreal, Paris, France

[21] Appl. No.: 09/068,964

[22] PCT Filed: May 20, 1997

[86] PCT No.: PCT/FR97/00885

§ 371 Date: May 20, 1998

§ 102(e) Date: May 20, 1998

[87] PCT Pub. No.: WO97/44004

PCT Pub. Date: Nov. 27, 1997

[30] Foreign Application Priority Data

May 23, 1996 [FR] France .................................. 96/06430

[51] Int. Cl.⁷ ...................................................... A61K 7/13
[52] U.S. Cl. .......................... 8/405; 8/414; 8/415; 8/428; 8/557; 8/558; 8/662; 8/675
[58] Field of Search ................. 8/405, 407, 425, 8/426, 428, 558, 557, 649, 662, 675, 414, 415

[56] References Cited

U.S. PATENT DOCUMENTS

| | | | |
|---|---|---|---|
| 3,915,921 | 10/1975 | Schlatzer et al. | 526/238.23 |
| 3,919,265 | 11/1975 | Bugaut et al. | 552/306 |
| 3,929,404 | 12/1975 | Kalopissis et al. | 8/407 |
| 3,930,865 | 1/1976 | Faust et al. | 430/260 |
| 4,023,926 | 5/1977 | Bugaut et al. | 8/407 |
| 4,046,786 | 9/1977 | Kalopissis et al. | 552/302 |
| 4,084,052 | 4/1978 | Bugaut et al. | 544/165 |
| 4,093,806 | 6/1978 | Kalopisis et al. | 544/165 |
| 4,112,155 | 9/1978 | Carel et al. | 8/558 |
| 4,145,299 | 3/1979 | Ford, Jr. et al. | 430/106 |
| 4,204,059 | 5/1980 | Bugaut et al. | 544/166 |
| 4,213,960 | 7/1980 | Grollier et al. | 424/47 |
| 4,260,749 | 4/1981 | Bugaut et al. | 544/166 |
| 4,402,977 | 9/1983 | Grollier et al. | 424/70.13 |
| 4,509,949 | 4/1985 | Huang et al. | 8/558 |
| 5,030,443 | 7/1991 | Varco et al. | 424/47 |
| 5,102,655 | 4/1992 | Yoshihara et al. | 8/426 |
| 5,685,882 | 11/1997 | Samain et al. | 8/411 |
| 5,989,295 | 11/1999 | De Le Mettrie et al. | 8/406 |

FOREIGN PATENT DOCUMENTS

| | | |
|---|---|---|
| 0 445 714 | 9/1991 | European Pat. Off. . |
| 0 503 507 | 9/1992 | European Pat. Off. . |
| 2 189 380 | 1/1974 | France . |
| 2 234 277 | 1/1975 | France . |
| 2 382 232 | 9/1978 | France . |
| 3 044 754 | 6/1981 | Germany . |
| 9 413 897 | 2/1996 | Germany . |
| 63-218614 | 9/1988 | Japan . |
| 1-213221 | 8/1989 | Japan . |
| 3-220114 | 9/1991 | Japan . |

OTHER PUBLICATIONS

English language translation of JP 63–218,614, pp. 1–17, Sep. 1988.
English language translation of JP 1–213,221, pp. 1–18, Aug. 1989.

*Primary Examiner*—Caroline D. Liott
*Attorney, Agent, or Firm*—Finnegan, Henderson, Farabow, Garrett & Dunner, L.L.P.

[57] ABSTRACT

The invention discloses a capillary dyeing composition comprising at least one direct dye, wherein the composition further comprises a cross-linked polymer with acrylic units and alkyl $C_{10}$–$C_{30}$ acrylate units. The invention also discloses the use of cross-linked polymer with acrylic units and alkyl $C_{10}$–$C_{30}$ acrylate units in or for the production of a capillary dyeing composition comprising at least one direct dye, to improve the tinctorial power of the composition, particularly after storage at below about 10° C., and in particular at about 4° C. The invention also discloses a method for preserving the tinctorial power of the composition, particularly after storage at below about 10° C., of a dyeing composition containing at least one direct dye, wherein an effective amount of the cross-linked polymer is added to the composition.

31 Claims, No Drawings

DIRECT CAPILLARY DYEING COMPOSITION COMPRISING A CROSS-LINKED POLYMER WITH ACRYLIC AND ALKYL $C_{10}$-$C_{30}$ ACRYLATE UNITS

The invention relates to a composition for dyeing the hair, comprising at least one direct dye and at least one crosslinked polymer containing acrylic units and $C_{10}$–$C_{30}$ alkyl acrylate units.

It is known to dye hair fibres with direct dye compositions according to a so-called "direct dyeing" process which consists in applying to the fibres dye molecules which have an affinity for the said fibres, in leaving them to stand on the fibres and then in rinsing the fibres. The resulting colorations are temporary or semi-permanent colorations depending on the nature of the interactions between the direct dyes and the hair fibre, and their desorption from the surface and/or from the core of the fibre.

In order to facilitate the application of such dye compositions to the hair, in particular to prevent them from running down the forehead and the face or beyond the point of application initially chosen, when they are applied or during the exposure time required for dyeing, the viscosity of the compositions is conventionally increased using crosslinked polyacrylic acid (thickener). However, dye compositions based on direct dyes and on crosslinked polyacrylic acid no longer prove to be sufficiently satisfactory as regards their dyeing properties after they have been stored for a certain period at a temperature below room temperature, for example below 10° C., and in particular at about 4° C. Thus, it is observed that compositions stored under such conditions give rise to a weaker rise of the direct dye on the hair and thus have an insufficient dyeing power.

The present invention aims to solve the above problem, i.e. to propose a means which makes it possible to preserve the dyeing power of dye compositions containing a direct dye, for compositions liable to be stored at low temperatures, in particular at temperatures below 10° C.

After considerable research conducted in this matter, the Applicant has now discovered that it is possible to preserve the dyeing power of direct dye compositions if an effective amount of a crosslinked polymer containing acrylic units and $C_{10}$–$C_{30}$ alkyl acrylate units is added to these compositions.

Even after relatively prolonged storage at temperatures below 10° C., and in particular close to 4° C., compositions with good dyeing power and whose rise on the hair is very satisfactory are obtained.

This discovery forms the basis of the present invention.

The subject of the present invention is thus a cosmetic composition for dyeing the hair, of the type comprising, in a cosmetically acceptable support which is suitable for dyeing, at least one direct dye, characterized in that it also comprises at least one crosslinked polymer containing acrylic units and $C_{10}$–$C_{30}$ alkyl acrylate units.

The subject of the present invention is also the use of a crosslinked polymer containing acrylic units and $C_{10}$–$C_{30}$ alkyl acrylate units in, or for the manufacture of, a direct dye composition for the hair comprising at least one direct dye, in order to improve the conservation of the dyeing power of the said composition, in particular after storage below about 10° C., and especially at about 4° C.

The invention also relates to a process for improving the conservation of the dyeing power, in particular after storage below about 10° C., and especially at about 4° C., of a dye composition for the hair comprising at least one direct dye, this process consisting in introducing an effective amount of at least one crosslinked polymer containing acrylic units and $C_{10}$–$C_{30}$ alkyl acrylate units into the said composition.

Lastly, the invention relates to a process for dyeing hair using the compositions with improved properties in accordance with the invention.

However, other characteristics, aspects, objects and advantages of the invention will become even more apparent on reading the description and the examples which follow.

According to the invention, the term acrylic units is understood to denote units of structure $$CH_2=\underset{R_1}{\overset{}{C}}-\underset{O}{\overset{\|}{C}}-OH$$

in which $R_1$ denotes H or $CH_3$ or $C_2H_5$, i.e. acrylic acid, methacrylic acid, or ethacrylic acid units.

The term alkyl acrylate units is also understood to denote units of structure:

$$CH_2=\underset{R_1}{\overset{}{C}}-\underset{O}{\overset{\|}{C}}-OR_2$$

in which $R_1$ denotes H or $CH_3$ or $C_2H_5$, i.e. acrylate, methacrylate or ethacrylate units, $R_2$ denoting a $C_{10}$–$C_{30}$, preferably $C_{12}$–$C_{22}$, alkyl radical.

The crosslinked polymer(s) containing acrylic units and $C_{10}$–$C_{30}$ alkyl acrylate units, which can be used in the context of the present invention, can more particularly denote a terpolymer of a mixture of monomers essentially comprising:
(a) an acrylic, methacrylic or ethacrylic, but preferably acrylic or methacrylic, acid,
(b) an acrylate of formula:

$$CH_2=\underset{R_1}{\overset{}{C}}-\underset{O}{\overset{\|}{C}}-OR_2$$

in which $R_1$ denotes H or $CH_3$ or $C_2H_5$, but preferably H or $CH_3$, and $R_2$ denotes an alkyl radical having from 10 to 30 carbon atoms, and preferably from 12 to 22 carbon atoms, and
(c) a crosslinking polymerizable monomer containing a group $$CH_2=C\big<$$

with at least one other polymerizable group in which the unsaturated bonds are not conjugated with each other.

Acrylates in accordance with the invention comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Crosslinking polymerizable monomers of the type (c) are, for example, and preferably, polyallyl ethers such as, in particular, polyallylsucrose and polyallylpentaerythritol.

Crosslinked polymers of this type are well known; they are prepared and described in U.S. Pat. Nos. 3,915,921 and 4,509,949.

According to the invention, it is more particularly possible to use (i) those which consist of 95 to 60% by weight of acrylic units, from 4 to 40% by weight of acrylate units and from 0.1 to 6% by weight of crosslinking monomer of type (c) or (ii) those which consist of 98 to 96% by weight of acrylic units, from 1 to 4% by weight of acrylate units and from 0.1 to 0.6% by weight of crosslinking monomer of type (c).

Among the abovementioned crosslinked polymers, the products sold by the company Goodrich under the trade names Pemulen TR1, Pemulen TR2, Carbopol 1342, and even more preferably Pemulen TR1, are most particularly preferred according to the invention.

The crosslinked polymers containing acrylic units and $C_{10}$–$C_{30}$ alkyl acrylate units described above are used in the dye composition according to the invention in proportions which can range from about 0.05 to about 5% by weight, and preferably from about 0.1 to about 3% by weight, relative to the total weight of the composition.

The direct dyes which can be used in the dye composition according to the present invention are direct dyes in the sense defined above, that is to say dyes which can be used in a standard direct dyeing process.

Among those used conventionally, mention may be made of nitrobenzene dyes such as nitrophenylenediamines, nitrodiphenylamines, nitroanilines, nitrophenols or nitrophenol ethers, nitropyridines, anthraquinone, mono- or diazo, triarylmethane, azine, acridine and xanthene dyes or alternatively metalliferous dyes.

The direct dyes more particularly preferred according to the invention are chosen from the following:

i) the nitrobenzene dyes of formula (I) below:

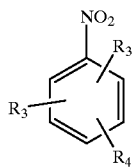

(I)

in which:
R$_3$ denotes an NH$_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals, R$_4$ denotes hydrogen, hydroxyl, alkoxy, mono- or polyhydroxyalkyloxy, or the same meanings denoted above for R$_3$, except for the disubstituted amino radical, R$_5$ denotes hydrogen, alkyl, nitro or halogen, ii) the anthraquinone dyes of formula (II) below:

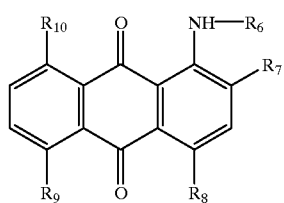

(II)

in which
R$_6$ denotes hydrogen or a monohydroxyalkyl or polyhydroxyalkyl radical, R$_7$ denotes hydrogen or an alkyl or alkoxy radical, R$_8$ denotes hydrogen or a hydroxyl, amino, monohydroxyalkylamino or polyhydroxyalkylamino radical R$_9$ and R$_{10}$, which may be identical or different, are hydrogen, hydroxyl or amino, iii) the azo dyes of formula (III) below:

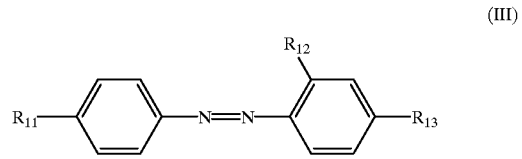

(III)

in which:
R$_{11}$ denotes a nitro or amino radical or an amino radical mono- or disubstituted with alkyls, R$_{12}$ denotes hydrogen or an alkyl radical, R$_{13}$ denotes an amino radical or an amino radical mono- or disubstituted with monohydroxyalkyls, it being understood that the alkyl and alkoxy radicals mentioned above in formulae (I), (II), and (III) are $C_1$–$C_4$ and that they can be linear or branched, and the cosmetically acceptable salts of all these compounds.

The term $C_1$–$C_4$ is understood to refer in particular to the methyl, ethyl, n-propyl, isopropyl, n-butyl, sec-butyl and tert-butyl radicals.

The expression cosmetically acceptable salts is understood more particularly to denote the hydrochlorides, hydrobromides and sulphates.

Even more advantageously, according to the present invention, it is preferred to use the following direct dyes:
1-amino-2-nitro-4-N-(β-hydroxyethyl)amino-5-methylbenzene,
1,4,5,8-tetraaminoanthraquinone,
1,4-bis-N-N'-[(β,γ-dihydroxypropyl)amino]-anthraquinone,
1,4,4-N-tris(β-hydroxyethyl)-1,4-diamino-2-nitrobenzene,
1-N-(β-hydroxyethyl)amino-2-nitro-4-aminobenzene,
1-hydroxy-3-nitro-4-aminobenzene,
1-hydroxy-3-nitro-4-N-(β-hydroxyethyl)aminobenzene,
1-β-hydroxyethyloxy-3-methylamino-4-nitrobenzene,
1-methylamino-2-nitro-5-β,γ-dihydroxypropyloxybenzene,
1-N-(β-aminoethyl)amino-2-nitro-4-β-hydroxyethyloxybenzene,
4-[N-ethyl-N-(β-hydroxyethyl)amino]-1-N-(β-hydroxyethyl)amino-2-nitrobenzene,
1-(4'-aminodiphenylazo)-2-methyl-4-N-bis(β-hydroxyethyl)aminobenzene,
1-methoxy-3-N-(β-aminoethyl)amino-4-nitrobenzene,
1-amino-2-nitro-4-N-(β-hydroxyethyl)aminobenzene,
1-amino-2-nitro-4-N-bis(β-hydroxyethyl)aminobenzene,
1,4-N-bis(β-hydroxyethyl)amino-2-nitrobenzene,
1-amino-2-N-(β-hydroxyethyl)amino-5-nitrobenzene,
1,4-diaminoanthraquinone,
and the cosmetically acceptable salts thereof.

These direct dyes, in salified or base form, are generally present in the dye composition according to the invention in proportions which can range from about 0.001 to about 10% by weight, and preferably from about 0.05 to about 5% by weight, relative to the total weight of the composition.

The cosmetically acceptable medium for the dyeing is an aqueous medium which can contain one or more organic solvents chosen, for example, from ethyl alcohol, isopropyl alcohol, benzyl alcohol and phenylethyl alcohol, or glycols or glycol ethers such as, for example, propylene glycol or its ethers such as, for example, propylene glycol monomethyl ether, butylene glycol, dipropylene glycol, ethylene glycol monomethyl, monoethyl and monobutyl ethers, and diethylene glycol alkyl ethers such as, for example, diethylene glycol monoethyl ether or monobutyl ether, in proportions of approximately between 0.5 and 20% by weight, and preferably approximately between 2 and 10% by weight, relative to the total weight of the composition.

Fatty amides such as mono- and diethanolamides of coconut-derived acids, of lauric acid or of oleic acid, at concentrations of approximately between 0.05 and 10% by weight can also be added to the composition according to the invention.

Surfactants that are well known in the state of the art and of anionic, cationic, nonionic, amphoteric or zwitterionic type or mixtures thereof can also be added to the composition according to the invention, preferably in a proportion of approximately between 0.1 and 50% by weight, and advantageously approximately between 1 and 20% by weight, relative to the total weight of the composition.

The said dye composition can also contain various common adjuvants such as antioxidants, fragrances, sequestering agents, dispersing agents, hair conditioners, preserving agents and opacifiers, as well as any other adjuvant usually used to dye the hair.

Needless to say, a person skilled in the art will take care to select the optional complementary compound(s) mentioned above such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 3 to 12 and preferably from 7 to 11 and even more preferably from 8.5 to 10, and for it be adjusted using basifying agents or acidifying agents that are previously well known. As basifying agents, mention may be made of aqueous ammonia, alkaline carbonates, alkanolamines, for example mono-, di- and triethanolamines and derivatives thereof, sodium hydroxide, potassium hydroxide, and compounds of formula:

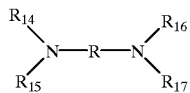

in which R is a propylene residue optionally substituted with a hydroxyl group or a $C_1$–$C_4$ alkyl radical; $R_{14}$, $R_{15}$, $R_{16}$ and $R_{17_1}$ simultaneously or independently of each other, represent a hydrogen atom or a $C_1$–$C_4$ alkyl or $C_1$–$C_4$ hydroxyalkyl radical.

The acidifying agents are conventionally inorganic or organic acids such as, for example, hydrochloric acid, tartaric acid, citric acid and phosphoric acid.

The composition applied to the hair can be in various forms, such as in the form of a liquid, a cream or a gel or in any other form which is suitable for dyeing the hair. In particular, it can be packaged under pressure in an aerosol can in the presence of a propellant and can form a mousse.

Another subject of the present invention relates to a process for dyeing the hair, by direct dyeing, which consists in applying a dye composition as defined above to wet or dry hair, then in leaving the said composition to act, preferably for 3 to 60 minutes approximately, in rinsing the hair, then optionally in washing it, then in rinsing it again and then in drying it.

It is also possible to leave the composition to act and then dry it.

Concrete examples illustrating the invention will now be given.

EXAMPLE 1

The following dyeing composition was prepared:
Direct dye (1)* . . . 0.1 g
Decyl alcohol oxyethylenated with 5.3 mol of ethylene oxide . . . 2.0 g
Lauric acid . . . 1.0 g
Diethylene glycol monobutyl ether . . . 5.0 g
Pemulen TR1 from Goodrich (acrylic acid/$C_{10}$–$C_{30}$ alkyl acrylates crosslinked copolymer) . . . 0.51 g
2-Amino-2-methyl-1-propanol . . . q.s. . . . pH. 9.5
Demineralized water . . . q.s.p. . . . 100 g
* dye (1): 1-amino-2-nitro-4-N-(β-hydroxyethyl)-amino-5-methylbenzene After 24 hours, the viscosity of this composition was measured using a Contrave viscometer at 25° C. The viscosity recorded was 200 cp.

This composition was then applied to locks of natural grey hair containing 90% white hairs and the composition was left to stand on the hair for 30 minutes. The locks were then rinsed with running water and dried.

The locks were dyed in a shade which, quantified in terms of the Munsell value (ASTM standard D 1535-68, which defines the colour: H denoting the shade or Hue, V denoting the intensity or Value, and C denoting the purity or Chromacity), on a Minolta CM 2002 calorimeter, was as follows: in H,V,C: 7.5 R 4.7/2.9.

The control locks (not dyed) had an H,V,C shade: 3.8 Y 5.7/1.6.

The composition prepared above was also stored for one month at a temperature of 4° C.

The composition thus stored was then applied to locks of hair of the same quality and according to the same procedure as above.

The shade of the locks dyed using this composition stored at 4° C. was as follows: in H,V,C: 7.9 R 4.7/2.8.

The change in colour between the locks dyed using the initial composition and those dyed using the composition stored for one month at a temperature of 4° C. was then quantified using the Nickerson equation which defines the colour variation indices: I=(C/5)×2ΔH+6ΔV+3ΔC (this equation being described in the publication: "Journal of the Optical Society of America", September 1944 Vol. 34, No. 9, pp.550–570).

Thus, the change in Colour $I_b$ (colour variation index between the locks dyed using the composition stored for one month at a temperature of 4° C. and that of the locks dyed using the initial composition) relative to the initial coloration $I_a$ (colour variation index of the locks dyed using the initial composition and that of the control locks), quantified in %, was 3.7%.

COMPARATIVE EXAMPLE 2

A dye composition similar to that of Example 1 was prepared, with a viscosity equal to that of Example 1, based on polymer of the prior art, but simply replacing the 0.51 g of Pemulen TRI by 0.57 g of Carbopol 980 from the company Goodrich (crosslinked polyacrylic acid of the prior art—MW 4,000,000).

Locks of natural hair containing 90% white hairs were dyed using the initial composition (i.e. before storage) and according to a procedure identical to that of Example 1, in a shade, expressed in terms of H,V,C, equal to: 8.1 R 4.9/2.9.

Locks of natural hair containing 90% white hairs were dyed using the same composition but stored for one month at 4° C. The shade obtained was:
H,V,C: 8.7R 4.8/2.8.

The ratio $I_b/I_a$ applied to this example, and quantified in %, was 8.5%.

Conclusion

After storage for one month at 4° C., the dye composition of Example 1 comprising a crosslinked polymer in accordance with the present invention has a dyeing power which is considerably superior to that of the dye composition of Example 2 comprising a crosslinked polymer of the prior art, since the degradation, which is expressed by the ratio $I_b/I_a$, quantified in %, is only 3.7% in the case of Example 1, whereas it is 8.5% in the case of Example 2.

EXAMPLE 3

The following dye composition was prepared:
Direct dye (2)* . . . 0.1 g
Decyl alcohol oxyethylenated with 5.3 mol of ethylene oxide . . . 2.0 g
Lauric acid . . . 1.0 g
Diethylene glycol monobutyl ether . . . 5.0 g
Pemulen TR1 from Goodrich (acrylic acid/$C_{10}$–$C_{30}$ alkyl acrylates crosslinked copolymer) . . . 0.54 g
2-Amino-2-methyl-1-propanol . . . q.s. . . . pH . . . 9.5
Demineralized water . . . q.s.p. . . . 100 g
* direct dye (2): 1,4,5,8-tetraaminoanthraquinone (at 30%, dispersed on lignosulphate).

After 24 hours, the viscosity of this composition was measured using a Contrave viscometer at 25° C. The viscosity recorded was 220 cp.

This composition was then applied to locks of permanent-waved grey hair containing 90% white hairs and the composition was left to stand on the hair for 30 minutes. The locks were then rinsed with running water and dried.

The locks were dyed in a shade which, quantified in terms of the Munsell value, was as follows, in H,V,C: 4.1 B 4.2/2.4.

The control locks (not dyed) had an H, V, C shade: 4.4 Y 5.9/1.6.

The abovementioned composition was then stored for one month at a temperature of 4° C.

The composition thus stored was then applied to locks of hair of the same quality and according to the same procedure as above.

The shade of the locks dyed using this composition stored at 4° C. was as follows, in terms of H, V, C: 2.1 B 4.4/2.2.

The ratio $I_b$ (colour variation index between the locks dyed using the composition stored for one month at a temperature of 4° C. and that of the locks dyed using the initial composition) to $I_a$ (colour variation index between the locks dyed using the initial composition and that of the control locks), quantified in %, was 9.8%.

COMPARATIVE EXAMPLE 4

A dye composition similar to that of Example 3 was prepared, with a viscosity equal to that of Example 3, based on polymer of the prior art, but simply replacing the 0.54 g of Pemulen TR1 by 0.67 g of Carbopol 2984 from the company Goodrich (crosslinked polyacrylic acid of the prior art—MW 3,000,000).

Locks of permanent-waved hair containing 90% white hairs were dyed using the initial composition (i.e. before storage) and according to a procedure identical to that of Example 3, in a shade, expressed in terms of H,V,C, equal to: 5.4 B 4.1/3.1.

Locks of permanent-waved hair containing 90% white hairs were dyed using the same composition but stored for one month at 4° C. The shade obtained was, in terms of H, V, C, equal to: 1.6 B 4.3/1.9.

The ratio $I_b/I_a$ applied to this example, and quantified in %, was 22.9%.

Conclusion:

After storage for one month at 4° C., the dye composition of Example 3 comprising a crosslinked polymer in accordance with the present invention has a dyeing power which is considerably superior to that of the dye composition of Example 4 comprising a crosslinked polymer of the prior art, since the degradation, which is expressed by the ratio $I_b/I_a$, quantified in %, is only 9.8% in the case of Example 3, whereas it is 22.9% in the case of Example 4.

EXAMPLE 5

The following dye composition was prepared:
Direct dye (3)* . . . 0.15 g
Decyl alcohol oxyethylenated with 5.3 mol of ethylene oxide . . . 2.0 g
Lauric acid . . . 1.0 g
Diethylene glycol monobutyl ether . . . 5.0 g
Pemulen TR1 from Goodrich (acrylic acid/$C_{10}$–$C_{30}$ alkyl acrylates crosslinked copolymer) . . . 0.52 g
2-Amino-2-methyl-1-propanol . . . q.s. . . . pH. 9.5
Demineralized water . . . q.s.p. . . . 100 g
*direct dye (3): 1,4-bis-N,N'-[(β,γ-dihydroxypropyl)amino]anthraquinone.

After 24 hours, the viscosity of this composition was measured using a Contrave viscometer at 25° C. The viscosity recorded was 210 cp.

This composition was then applied to locks of natural grey hair containing 90% white hairs and was left to stand on the hair for 30 minutes. The locks were then rinsed with running water and dried.

The locks were dyed in a shade which, quantified in terms of the Munsell value, was as follows, in terms of H,V,C: 5.9 GY 5.1/1.0.

The control locks (not dyed) had an H,V,C shade: 3.8Y 5.7/1.6.

The abovementioned composition was then stored for one month at a temperature of 4° C.

The composition thus stored was then applied to locks of hair of the same quality and according to the same procedure as above.

The shade of the locks dyed using this composition stored at 4° C. was as follows, in terms of H, V, C: 1.2 GY 5.1/1.1.

The ratio $I_b$ (colour variation index between the locks dyed using the composition stored for one month at a temperature of 4° C. and that of the locks dyed using the initial composition) to $I_a$ (colour variation index between the locks dyed using the initial composition and that of the control locks), quantified in %, was 16.6%.

COMPARATIVE EXAMPLE 6

A dye composition similar to that of Example 5 was prepared, with a viscosity equal to that of Example 5, based on polymer of the prior art, but simply replacing the 0.52 g of Pemulen TRI by 0.65 g of Carbopol 2984 from the company Goodrich (crosslinked polyacrylic acid of the prior art).

Locks of natural hair containing 90% white hairs were dyed using the initial composition (i.e. before storage) and according to a procedure identical to that of Example 5, in a shade, expressed in terms of H, V, C, equal to: 6.6 GY 5.2/1.0.

Locks of natural hair containing 90% white hairs were dyed using the same composition but stored for one month at 4° C. The shade obtained was, in terms of H,V,C, equal to: 10.0 Y 5.4/1.2.

The ratio $I_b/I_a$ applied to this example, and quantified in %, was 34.2%.

Conclusion

After storage for one month at 4° C., the dye composition of example 5 comprising a crosslinked polymer in accordance with the present invention has a dyeing power which is considerably superior to that of the dye composition of example 6 comprising a crosslinked polymer of the prior art, since the degradation, which is expressed by the ratio $I_b/I_a$, quantified in %, is only 16.6% in the case of Example 5, whereas it is 34.2% in the case of Example 6.

What is claimed is:

1. A composition comprising, in a cosmetically acceptable support suitable for dyeing, at least one direct dye and at least one crosslinked polymer containing acrylic residue units of the structure $$CH_2=\underset{R_1}{C}-\underset{O}{\overset{\|}{C}}-OH$$

in which $R_1$ denotes H, $CH_3$ or $C_2H_5$, and $C_{10}-C_{30}$ alkyl acrylate residue units, wherein said composition is a direct dyeing composition for the hair, and wherein said at least one direct dye is chosen from:

a nitrobenzene dye of formula (I):

(I)

in which:

$R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals, $R_4$ denotes hydrogen, hydroxyl, alkoxy, mono- or polyhydroxyalkyloxy, an $NH_2$ radical, or an amino radical monosubstituted with an alkyl, monohydroxyalkyl, polyhydroxyalkyl or aminoalkyl radical, $R_5$ denotes hydrogen, alkyl, nitro or halogen, wherein said alkyl and alkoxy radicals are $C_1-C_4$ and are linear or branched;

a cosmetically acceptable salt of said nitrobenzene dye;

an anthraquinone dye of formula (II):

(II)

in which:

$R_6$ denotes hydrogen or a monohydroxyalkyl or polyhydroxyalkyl radical, $R_7$ denotes hydrogen or an alkyl or alkoxy radical, $R_8$ denotes hydrogen or a hydroxyl, amino, monohydroxyalkylamino or polyhydroxyalkylamino radical, $R_9$ and $R_{10}$ independently are hydrogen, hydroxyl or amino, wherein said alkyl and alkoxy radicals are $C_1-C_4$ and are linear or branched:

a cosmetically acceptable salt of said anthraquinone dye;

an azo dye of formula (III):

(III)

in which:

$R_{11}$ denotes a nitro or amino radical or an amino radical mono- or disubstituted with alkyls, $R_{12}$ denotes hydrogen or an alkyl radical, $R_{13}$ denotes an amino radical or an amino radical mono- or disubstituted with monohydroxyalkyls, wherein said alkyl radicals are $C_1-C_4$ and are linear or branched; and a cosmetically acceptable salt of said azo dye.

2. A composition according to claim 1, wherein said at least one crosslinked polymer comprises:

(a) residue units of one of an acrylic, methacrylic or ethacrylic acid, (b) residue units of an acrylate of formula:

$$CH_2=\underset{R_1}{C}-\underset{O}{\overset{\|}{C}}-OR_2$$

in which:

$R_1$ denotes H or $CH_3$ or $C_2H_5$, and $R_2$ denotes an alkyl radical having from 10 to 30 carbon atoms, and, (c) residue units of a crosslinking polymerizable monomer containing a group

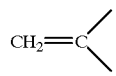

and also containing at least one other polymerizable group wherein the unsaturated bonds in said

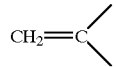

group and said at least one other polymerizable group are not conjugated with each other.

3. A composition according to claim 2, wherein at least one of the following conditions is true:
   (1) said at least one crosslinked polymer is a terpolymer, and wherein said terpolymer contains:
      (a) residue units of one of acrylic or methacrylic acid;
   (2) $R_1$ denotes H or $CH_3$;
   (3) $R_2$ denotes a $C_{12}$–$C_{22}$ alkyl radical; and
   (4) said crosslinking polymerizable monomer is a polyallyl ether.

4. A composition according to claim 3, wherein said polyallyl ether is selected from polyallylsucrose and polyallylpentaerythritol.

5. A composition according to claim 3 wherein said terpolymer contains:
   (a) residue units of an acrylic acid
   (b) residue units of an acrylate of formula:

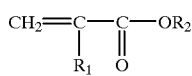

in which:
   $R_1$ denotes H or $CH_3$, and
   $R_2$ denotes an alkyl radical having from 12 to 22 carbon atoms, and
   (c) residue units of a polyallyl ether.

6. A composition according to claim 2, wherein said residue units (a) are present in an amount ranging from 60 to 95% by weight, said residue units (b) are present in an amount ranging from 4 to 40% by weight, and said residue units (c) are present in an amount ranging from 0.1 to 6% by weight, relative to the total weight of the crosslinked polymer.

7. A composition according to claim 2, wherein said residue units (a) are present in an amount ranging from 96 to 98% by weight, said residue units (b) are present in an amount ranging from 1 to 4% by weight, and said residue units (c) are present in an amount ranging from 0.1 to 0.6% by weight, relative to the total weight of the crosslinked polymer.

8. A composition according to claim 1, wherein said at least one crosslinked polymer is present in an amount ranging from 0.05 to 5% by weight relative to the total weight of said composition.

9. A composition according to claim 8, wherein said at least one crosslinked polymer is present in an amount ranging from 0.1 to 3% by weight relative to the total weight of said composition.

10. A composition according to claim 1, wherein said at least one direct dye is 1,4-bis-N,N'-[(β,γ-dihydroxypropyl)amino]anthraquinone.

11. A composition according to claim 1, wherein said cosmetically acceptable salt of said nitrobenzene dye is selected from hydrochlorides, hydrobromides and sulphates.

12. A composition according to claim 1, wherein said cosmetically acceptable salt of said anthraquinone dye is selected from hydrochlorides, hydrobromides and sulphates.

13. A composition according to claim 1, wherein said cosmetically acceptable salt of said azo dye is selected from hydrochlorides, hydrobromides and sulphates.

14. A composition according to claim 1, wherein said at least one direct dye is present, in salified or base form, in an amount ranging from 0.001 to 10% by weight, relative to the total weight of said composition.

15. A composition according to claim 1, wherein said at least one direct dye is present, in salified or base form, in an amount ranging from 0.5 to 5% by weight, relative to the total weight of said composition.

16. A composition according to claim 1, wherein said cosmetically acceptable support suitable for dyeing is an aqueous support comprising water or water and at least one organic solvent selected from alcohols, glycols and glycol ethers.

17. A composition according to claim 16, wherein said cosmetically acceptable support suitable for dyeing is an aqueous medium which contains at least one organic solvent in an amount ranging from 0.5 to 20% by weight relative to the total weight of said composition.

18. A composition according to claim 17, wherein said cosmetically acceptable support suitable for dyeing is an aqueous medium which can contains at least one organic solvent in an amount ranging from 2 to 10% by weight relative to the total weight of said composition.

19. A composition according to claim 1, wherein said composition further comprises at least one adjuvant.

20. A composition according to claim 1, wherein said composition has a pH ranging from 3 to 12.

21. A composition according to claim 20, wherein said composition has a pH ranging from 7 to 11.

22. A composition according to claim 21, wherein said composition has a pH ranging from 8.5 to 10.

23. A composition according to claim 1, wherein said composition is in the form of a liquid, a cream, a gel, or any other form suitable for dyeing hair.

24. A composition according to claim 1, wherein said composition is packaged under pressure in an aerosol can in the presence of a propellant.

25. A process of improving the conservation of the dyeing power of a direct dye composition by including in said composition an effective amount of at least one crosslinked polymer containing acrylic residue units of the structure

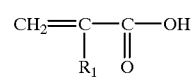

in which $R_1$ denotes H, $CH_3$ or $C_2H_5$, and $C_{10}$–$C_{30}$ alkyl acrylate residue units, and wherein said at least one direct dye is chosen from:

a nitrobenzene dye of formula (I):

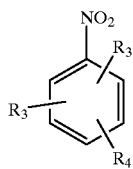
(I)

in which:
- $R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals,
- $R_4$ denotes hydrogen, hydroxyl, alkoxy, mono- or polyhydroxyalkyloxy, an $NH_2$ radical, or an amino radical monosubstituted with an alkyl, monohydroxyalkyl, polyhydroxyalkyl or aminoalkyl radical,
- $R_5$ denotes hydrogen, alkyl, nitro or halogen,
- wherein said alkyl and alkoxy radicals are $C_1$–$C_4$ and are linear or branched;
- a cosmetically acceptable salt of said nitrobenzene dye;
an anthraquinone dye of formula (II):

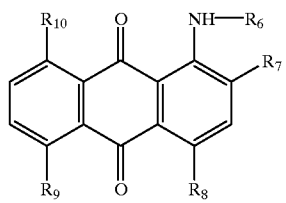
(II)

in which:
- $R_6$ denotes hydrogen or a monohydroxyalkyl or polyhydroxyalkyl radical,
- $R_7$ denotes hydrogen or an alkyl or alkoxy radical,
- $R_8$ denotes hydrogen or a hydroxyl, amino, monohydroxyalkylamino or polyhydroxyalkylamino radical,
- $R_9$ and $R_{10}$ independently are hydrogen, hydroxyl or amino,
- wherein said alkyl and alkoxy radicals are $C_1$–$C_4$ and are linear or branched;
- a cosmetically acceptable salt of said anthraquinone dye;
an azo dye of formula (III):

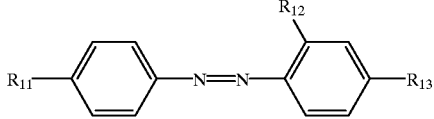
(III)

in which:
- $R_{11}$ denotes a nitro or amino radical or an amino radical mono- or disubstituted with alkyls,
- $R_{12}$ denotes hydrogen or an alkyl radical,
- $R_{13}$ denotes an amino radical or an amino radical mono- or disubstituted with monohydroxyalkyls, wherein said alkyl radicals are $C_1$–$C_4$ and are linear or branched; and
a cosmetically acceptable salt of said azo dye.

26. A process according to claim 25, of improving the conservation of the dyeing power of a direct dye composition after storage at low temperatures.

27. A process for dyeing hair by direct dyeing, comprising: applying to said hair when wet or dry an effective amount of a composition comprising, in a cosmetically acceptable support suitable for dyeing, at least one direct dye and at least one crosslinked polymer containing acrylic residue units of the structure

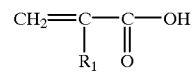

in which $R_1$ denotes H, $CH_3$ or $C_2H_5$, and $C_{10}$–$C_{30}$ alkyl acrylate residue units, and
wherein said at least one direct dye is chosen from:
a nitrobenzene dye of formula (I):

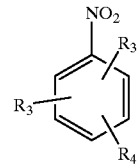
(I)

in which:
- $R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals,
- $R_4$ denotes hydrogen, hydroxyl, alkoxy, mono- or polyhydroxyalkyloxy, an $NH_2$ radical, or an amino radical monosubstituted with an alkyl, monohydroxyalkyl, polyhydroxyalkyl or aminoalkyl radical,
- $R_5$ denotes hydrogen, alkyl, nitro or halogen,
- wherein said alkyl and alkoxy radicals are $C_1$–$C_4$ and are linear or branched;
- a cosmetically acceptable salt of said nitrobenzene dye;
an anthraquinone dye of formula (II):

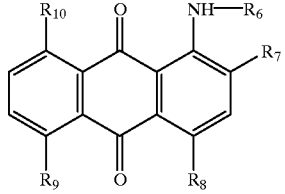
(II)

in which:
- $R_6$ denotes hydrogen or a monohydroxyalkyl or polyhydroxyalkyl radical,
- $R_7$ denotes hydrogen or an alkyl or alkoxy radical,
- $R_8$ denotes hydrogen or a hydroxyl, amino, monohydroxyalkylamino or polyhydroxyalkylamino radical,
- $R_9$ and $R_{10}$ independently are hydrogen, hydroxyl or amino, wherein said alkyl and alkoxy radicals are $C_1-C_4$ and are linear or branched;

a cosmetically acceptable salt of said anthraquinone dye;

an azo dye of formula (III):

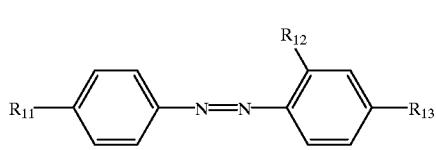

(III)

in which:

$R_{11}$ denotes a nitro or amino radical or an amino radical mono- or disubstituted with alkyls, $R_{12}$ denotes hydrogen or an alkyl radical, $R_{13}$ denotes an amino radical or an amino radical mono- or disubstituted with monohydroxyalkyls, wherein said alkyl radicals are $C_1-C_4$ and are linear or branched; and a cosmetically acceptable salt of said azo dye.

28. A process according to claim 27, further comprising the steps, after said applying step, of leaving said composition on said hair for a period of time; rinsing said hair; optionally washing and rinsing said hair; and drying said hair.

29. A process according to claim 28, wherein said composition is left on said hair for a period of time ranging from 3 to 60 minutes.

30. A process for dyeing hair by direct dyeing, comprising: applying to said hair when wet an effective amount of a composition comprising, in a cosmetically acceptable support suitable for dyeing, at least one direct dye and at least one crosslinked polymer containing acrylic residue units of the structure

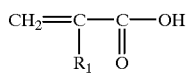

in which $R_1$ denotes H, $CH_3$ or $C_2H_5$, and $C_{10}-C_{30}$ alkyl acrylate residue units, and wherein said at least one direct dye is chosen from:

a nitrobenzene dye of formula (I):

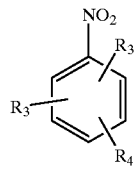

(I)

in which:

$R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals, $R_4$ denotes hydrogen, hydroxyl, alkoxy, mono- or polyhydroxyalkyloxy, an $NH_2$ radical, or an amino radical monosubstituted with an alkyl, monohydroxyalkyl, polyhydroxyalkyl or aminoalkyl radical, $R_5$ denotes hydrogen, alkyl, nitro or halogen, wherein said alkyl and alkoxy radicals are $C_1-C_4$ and are linear or branched;

a cosmetically acceptable salt of said nitrobenzene dye;

an anthraquinone dye of formula (II):

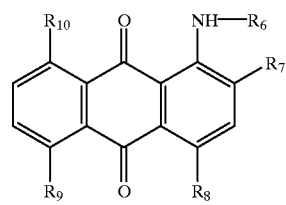

(II)

in which:

$R_6$ denotes hydrogen or a monohydroxyalkyl or polyhydroxyalkyl radical, $R_7$ denotes hydrogen or an alkyl or alkoxy radical, $R_8$ denotes hydrogen or a hydroxyl, amino, monohydroxyalkylamino or polyhydroxyalkylamino radical, $R_9$ and $R_{10}$ independently are hydrogen, hydroxyl or amino, wherein said alkyl and alkoxy radicals are $C_1-C_4$ and are linear or branched;

a cosmetically acceptable salt of said anthraquinone dye;

an azo dye of formula (III):

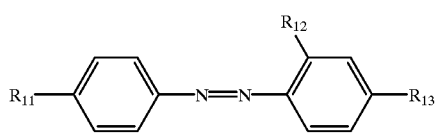

(III)

in which:

$R_{11}$ denotes a nitro or amino radical or an amino radical mono- or disubstituted with alkyls, $R_{12}$ denotes hydrogen or an alkyl radical, $R_{13}$ denotes an amino radical or an amino radical mono- or disubstituted with monohydroxyalkyls, wherein said alkyl radicals are $C_1-C_4$ and are linear or branched; and a cosmetically acceptable salt of said azo dye; and drying said hair.

31. A process according to claim 30, further comprising the step of waiting a period of time after said applying step and before said drying step—

* * * * *

UNITED STATES PATENT AND TRADEMARK OFFICE
CERTIFICATE OF CORRECTION

PATENT NO. : 6,136,042
DATED : October 24, 2000
INVENTOR(S) : Mireille Maubru

It is certified that error appears in the above-identified patent and that said Letters Patent is hereby corrected as shown below:

In the structure of formula (I) in:

claim 1, col. 9;

claim 25, col. 13;

claim 27, col. 14; and claim 30, col. 15,

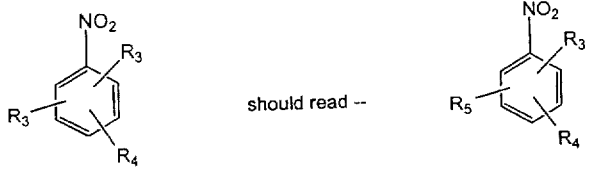

In claim 1, col. 10, line 25, "branched:" should read --branched;--.

Signed and Sealed this

Twenty-second Day of May, 2001

Attest:

NICHOLAS P. GODICI

Attesting Officer

Acting Director of the United States Patent and Trademark Office